US011185639B2

(12) United States Patent
Renstad et al.

(10) Patent No.: US 11,185,639 B2
(45) Date of Patent: Nov. 30, 2021

(54) WASTE CONTAINER FOR A MEDICAMENT DELIVERY DEVICE, AND A MEDICAMENT DELIVERY DEVICE FOR DISPOSAL IN THE WASTE CONTAINER

(71) Applicant: SHL Medical AG, Zug (CH)

(72) Inventors: Rasmus Renstad, Stockholm (SE); Daniel Säll, Segeltorp (SE)

(73) Assignee: SHL MEDICAL AG, Zug (CH)

( * ) Notice: Subject to any disclaimer, the term of this patent is extended or adjusted under 35 U.S.C. 154(b) by 25 days.

(21) Appl. No.: 16/469,696

(22) PCT Filed: Nov. 14, 2017

(86) PCT No.: PCT/EP2017/079186
§ 371 (c)(1),
(2) Date: Jun. 14, 2019

(87) PCT Pub. No.: WO2018/108412
PCT Pub. Date: Jun. 21, 2018

(65) Prior Publication Data
US 2020/0078531 A1  Mar. 12, 2020

(30) Foreign Application Priority Data
Dec. 16, 2016 (EP) ..................... 16204747

(51) Int. Cl.
*A61M 5/32* (2006.01)
*A61B 50/36* (2016.01)
*A61B 50/30* (2016.01)

(52) U.S. Cl.
CPC ....... *A61M 5/3205* (2013.01); *A61B 50/3001* (2016.02); *A61B 50/362* (2016.02)

(58) Field of Classification Search
CPC .............. A61M 5/3205; A61B 50/362; A61B 50/3001; A61B 2050/364; A61B 50/36
(Continued)

(56) References Cited

U.S. PATENT DOCUMENTS 4,553,687 A * 11/1985 Harkins .................. A61M 5/32
225/93
4,580,688 A   4/1986 Harris et al.
(Continued)

FOREIGN PATENT DOCUMENTS

| CN | 104874052 A | 9/2015 |
| TW | M417926 U1 | 12/2011 |
| WO | 2016169799 A1 | 10/2016 |

OTHER PUBLICATIONS

Search Report issued in Taiwanese Patent Application No. 106140506 dated Feb. 21, 2019.
(Continued)

*Primary Examiner* — Steven A. Reynolds
(74) *Attorney, Agent, or Firm* — McDonnell Boehnen Hulbert & Berghoff LLP

(57) ABSTRACT

A waste container (10) for medicament delivery devices, which waste container (10) comprises, a first compartment (12), a second compartment (14), a receiving compartment (22) for accommodating a medicament delivery device inserted into the waste container (10), a separation tool (24) for interacting with a medicament delivery device, and wherein the separation tool (24) is arranged to separate a first part (52) from a second part (54), of a medicament delivery device, accommodated in the receiving compartment (22), such that the first part (52) is stored in the first compartment (12) and the second part (54) is stored in the second compartment (14).

19 Claims, 7 Drawing Sheets

(58) Field of Classification Search
USPC .................................................. 206/366, 370
See application file for complete search history.

(56) References Cited

U.S. PATENT DOCUMENTS

| | | | |
|---|---|---|---|
| 5,090,564 A | | 2/1992 | Chimienti |
| 5,193,678 A | * | 3/1993 | Janocik ............ A61B 17/06161 |
| | | | 206/363 |
| 5,277,312 A | * | 1/1994 | Vumbaca .............. A61M 5/002 |
| | | | 206/366 |
| 5,394,982 A | | 3/1995 | Sawaya |
| 5,409,112 A | * | 4/1995 | Sagstetter ........... A61M 5/3205 |
| | | | 206/366 |
| 5,603,404 A | * | 2/1997 | Nazare ................ A61B 50/362 |
| | | | 206/1.5 |
| 6,247,592 B1 | * | 6/2001 | Racicot .............. A61M 5/3205 |
| | | | 206/366 |
| 6,253,916 B1 | * | 7/2001 | Bickel ................ A61M 5/3205 |
| | | | 206/366 |
| 10,086,416 B2 | * | 10/2018 | Maness ................ A61B 50/36 |

OTHER PUBLICATIONS

Chinese Office Action for CN App. No. 201780074852.7, dated Nov. 30, 2020.

* cited by examiner

WASTE CONTAINER FOR A MEDICAMENT DELIVERY DEVICE, AND A MEDICAMENT DELIVERY DEVICE FOR DISPOSAL IN THE WASTE CONTAINER

CROSS REFERENCE TO RELATED APPLICATIONS

The present application is a U.S. National Phase Application pursuant to 35 U.S.C. § 371 of International Application No. PCT/EP2017/079186 filed Nov. 14, 2017, which claims priority to European Patent Application No. 16204747.6 filed Dec. 16, 2016. The entire disclosure contents of these applications are hereby incorporated by reference into the present application.

TECHNICAL FIELD

The present disclosure relates to waste container for a medicament delivery device and to a medicament delivery device for disposal in the waste container. More in particular, the disclosure relates to a recycling system for separating two recyclable parts of a medicament delivery device and for storing the parts in different compartments of the waste container.

BACKGROUND

The widespread use of medicament delivery devices for self-treatment places demands on methods and equipment to handle the spent medicament delivery devices. One such piece of equipment is a type of waste container, often called a sharps bin, which may be placed in the user's home. Since the medicament delivery device may comprise potentially hazardous parts, such as injection needles and glass containers holding remains of drugs, the user is requested to discard the device in a sharps bin as soon as possible after use. The sharps bin serves to keep the hazardous parts out of harm's way until they are taken care of by professionals.

An example of a prior art sharps bin is disclosed by WO2016/169799. The disclosed sharps bin is intended to collect data from a discarded medicament delivery device. The discarded device comprises an electronics unit which unlocks the sharps bin and allows disposal of the device in the bin. The sharps bin is in turn arranged with a monitoring unit which collects the data from the discarded device. The whole device is stored in one compartment of the sharps bin.

Mass consumption puts an enormous pressure on the world's environment. In addition, medicament delivery devices may comprise parts which may be re-used, or which should be recycled in a manner different from the hazardous parts. Consequently, there is a need for recycling systems that handle the disposal of medicament delivery devices in a more sustainable and affordable manner.

SUMMARY

In view of the above, a general object of the present disclosure is to provide a waste container for separating two recyclable parts of a medicament delivery device and for storing the parts in different compartments of the waste container. An additional object of the present disclosure is to provide a medicament delivery device comprising two parts that may be separated by disposal in such a waste container.

The following definitions may be used herein:
In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Further, the term "longitudinal", with or without "axis", refers to a direction or an axis through the device or components thereof in the direction of the longest extension of the device or the component.

The term "lateral", with or without "axis", refers to a direction or an axis through the device or components thereof in the direction of the broadest extension of the device or the component. "Lateral" may also refer to a position to the side of a "longitudinally" elongated body.

In a similar manner, the terms "radial" or "transversal", with or without "axis", refers to a direction or an axis through the device or components thereof in a direction generally perpendicular to the longitudinal direction, e.g. "radially outward" would refer to a direction pointing away from the longitudinal axis.

Also, if nothing else is stated, in the following description wherein the mechanical structure of the device and the mechanical interconnection of its components is described, the device is in an initial non-activated or non-operated state.

According to a main aspect of the present disclosure there is provided a waste container for medicament delivery devices, which waste container comprises, a first waste compartment, a second waste compartment, a receiving compartment for receiving a medicament delivery device inserted into the waste container, a separation tool for interacting with a medicament delivery device, and wherein the separation tool is arranged to separate a first part from a second part, of a medicament delivery device received in the receiving compartment, such that the first part is stored in the first waste compartment and the second part is stored in the second waste compartment.

According to another aspect of the present disclosure, the receiving compartment and the separation tool are movable in relation to each other such that interaction between the separation tool and a medicament delivery device received in the receiving compartment separates the first part from the second part.

According to another aspect of the present disclosure, the receiving compartment is movable relative to the separation tool, and wherein the separation tool is fixed in relation to the waste container.

According to another aspect of the present disclosure, movement of the receiving compartment towards the separation tool moves a medicament delivery device, received in the receiving compartment, towards the cutting tool.

According to another aspect of the present disclosure, the receiving compartment is fixed relative to waste container, and wherein the separation tool is movable relative receiving compartment.

According to another aspect of the present disclosure, movement of the separation tool towards the receiving compartment is a movement of the separation tool towards a medicament delivery device received in the receiving compartment.

According to another aspect of the present disclosure, the separation tool is a cutting tool.

According to another aspect of the present disclosure, the separation tool is a wedge-like member.

According to another aspect of the present disclosure, the waste container further comprises a removable lid, and the receiving compartment and the separation tool are arranged in the lid.

According to a further main aspect of the present disclosure there is provided a medicament delivery device for disposal in the waste container according to the above, wherein the medicament delivery device comprises a first part attached to a second part, which first part and second part are separable from each other by disposal of the medicament delivery device in said waste container.

According to another aspect of the present disclosure, the first part and the second part are attached to each other by a breakable member.

According to another aspect of the present disclosure, the breakable member is a label.

According to another aspect of the present disclosure, the breakable member is a snap-fit member.

According to another aspect of the present disclosure, the first part comprises a medicament delivery member and a medicament container, and the second part comprises an electronics unit.

An advantage of the present disclosure is that a medicament delivery device containing different kinds of components may be conveniently disposed of, and the parts may be recycled separately, without compromising the security of the persons handling the medicament delivery device after disposal, e.g. by separately storing injection needles and medicament containers. In addition, parts that may be reused may be stored separately for later processing, and parts that are potentially environmentally damaging, e.g. parts containing batteries, may be stored separately and disposed of in an appropriate manner.

DETAILED DESCRIPTION

An embodiment of the present disclosure will be described below, with references being made to the drawings.

Figure 1:
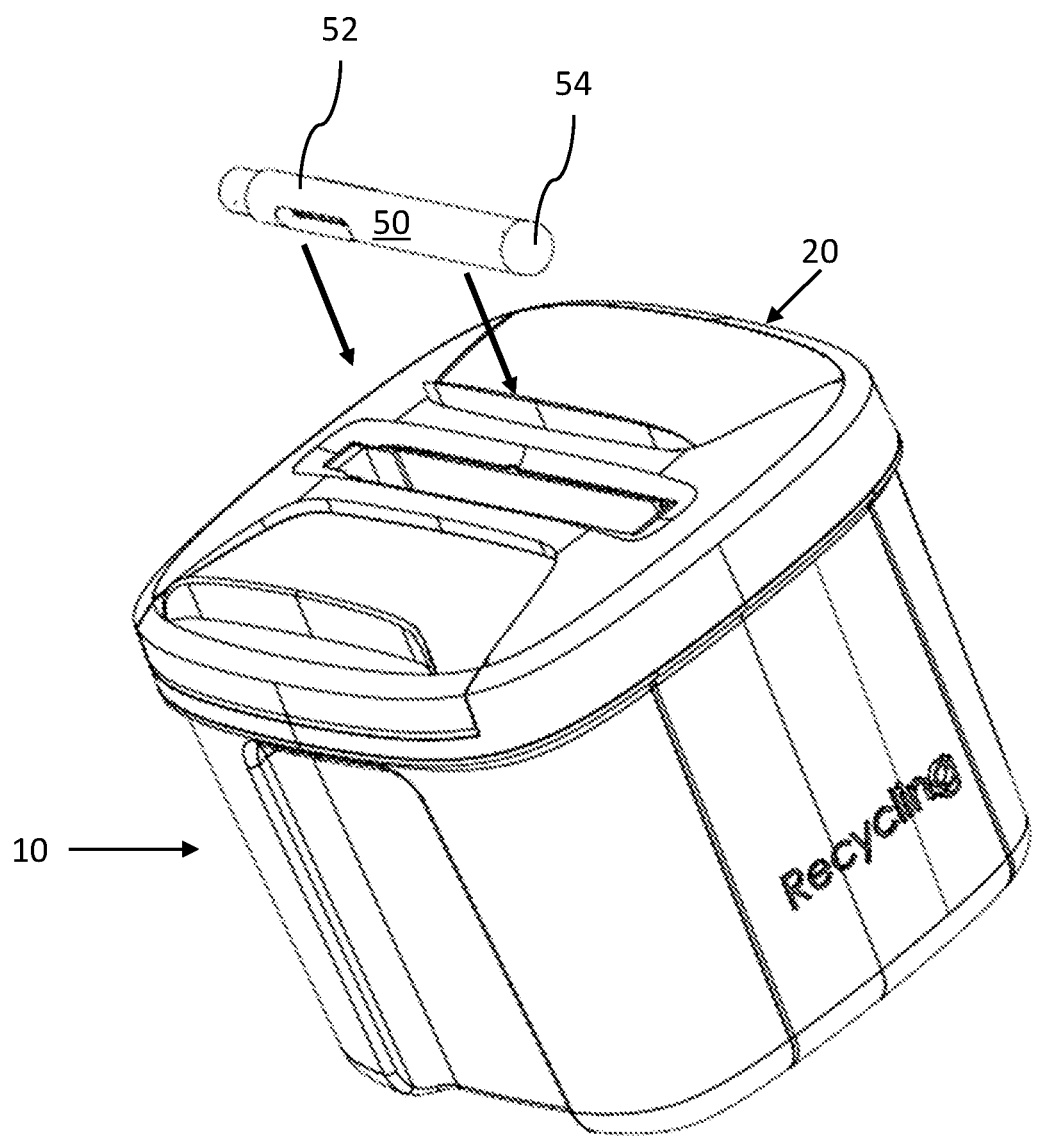
FIG. 1 a perspective view of a waste container and a medicament delivery device according to present disclosure FIG. 2 a top-side view of the waste container and the medicament delivery device of FIG. 1

FIG. 1 shows a perspective view of a waste container 10, and a longitudinally elongated medicament delivery device 50, according to the present disclosure. The medicament delivery device comprises at least a first part 52 and a second part 54, which need to be separated when the medicament delivery device is to be recycled. The waste container 10 comprises a first compartment 12 and a second compartment 14. The first and the second compartments are configured to receive the first part 52 and the second part 54, respectively, of the medicament delivery device 50, after it has been disposed in the waste container 10. The second compartment 14 is detachable from the waste container 10.

Figure 3:
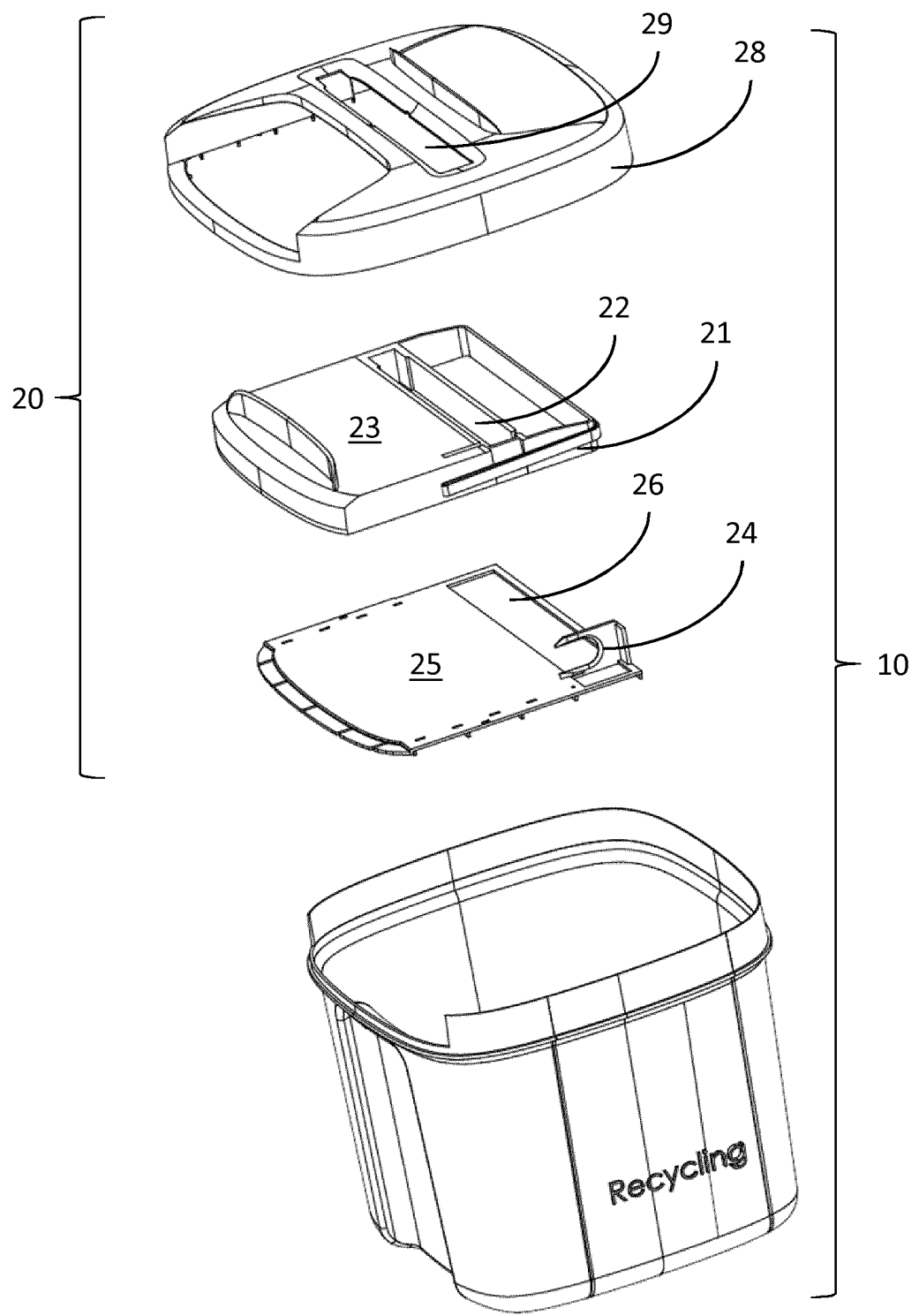
FIG. 3 an exploded view of the waste container of FIG. 1

The waste container 10 further comprises a removable lid assembly 20, FIG. 3. When assembled with the waste container 10, the lid assembly seals the first compartment 12 and the second compartment 14 such that any contents are kept safely inside. The lid assembly 20 comprises a receiving compartment 22 and a separation tool 24, for separating the first part 52, of the medicament delivery device 50, from the second part 54. A top lid 28 covers the receiving compartment 22 and the separation tool 24. The top lid 28 further comprises a longitudinally elongated first slot 29 for inserting the medicament delivery device 50 into the receiving compartment 22. When assembled with the waste container 10, the top lid 28 is fixed in relation to the first compartment 12 and the second compartment 24.

The receiving compartment 22 is a longitudinally elongated through-hole, formed in a tray 23. The tray 23 is positioned above a cover plate 25 and below the top lid 28. The separation tool 24 is arranged on the cover plate 25 at a longitudinally elongated second slot 26 formed in the cover plate 25.

Figure 2:
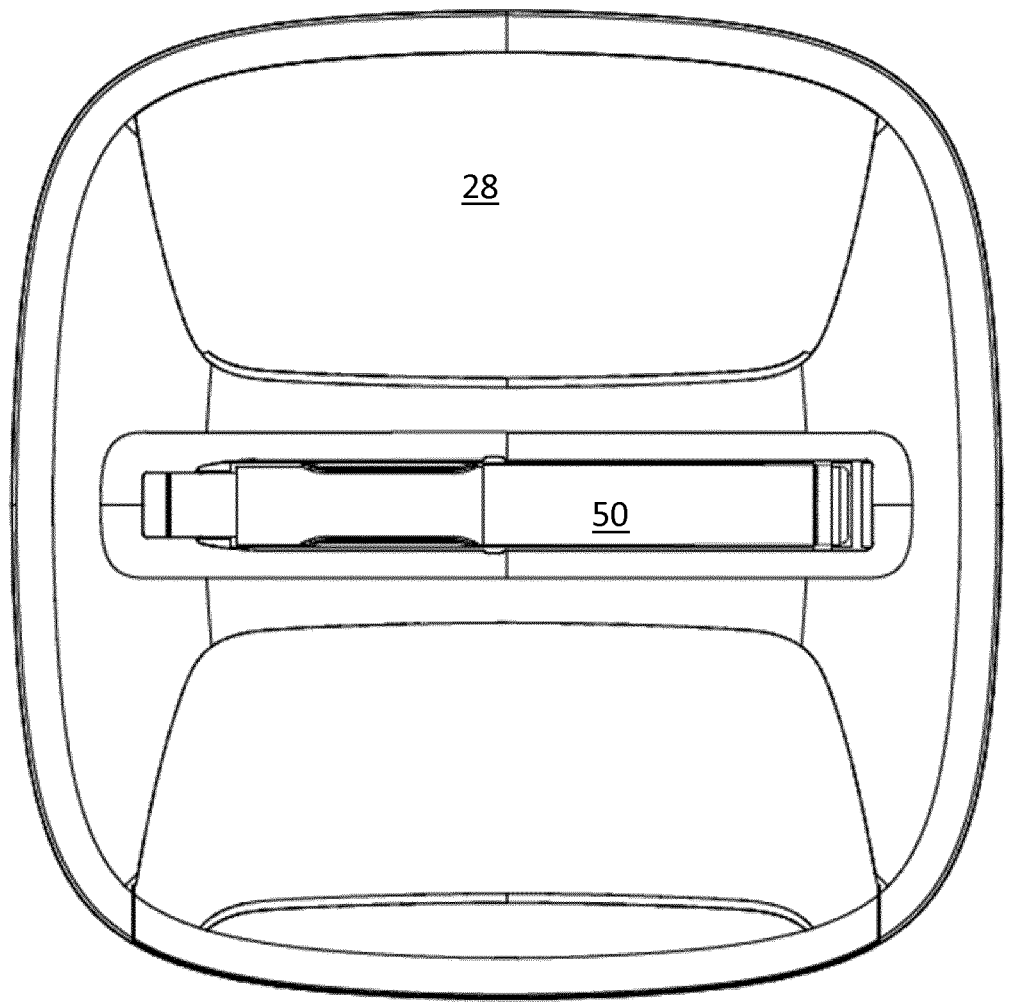

The tray 23, and thus the receiving compartment 22, is movable relative to the cover plate 25, and thus relative to the separation tool 24, between a first position and a second position. In the first position, the receiving compartment 22 is aligned with the first slot 29 of the top lid 28 such that a medicament delivery device 50 that is inserted, from above, into the first slot 29 is accommodated in the receiving compartment 22. In the exemplified embodiment, the medicament delivery device 50 is inserted laterally into the first slot 29 and the receiving compartment 22. Longitudinal insertion is a conceivable alternative. Also, the movement from the first position to the second position is a lateral movement with regard to the medicament delivery device 50. The first slot 29 and the receiving compartment 22 are shaped according to a shape of the medicament delivery device 50 so that the medicament delivery device 50 may only be accommodated in the receiving compartment 22 when correctly oriented with the receiving compartment 22, FIG. 2. In the second position, the receiving compartment 22 is aligned with the second slot 26 of the cover plate 25 such that a medicament delivery device accommodated in the receiving compartment 22 may fall through the second slot into the first compartment 12 and the second compartment 24 below, as will be described in more detail.

The separation tool 24 is positioned at a predetermined longitudinal position along the second slot 26, and in relation to the receiving compartment 22, such that it is aligned with an interface between the first part 52 and the second part 54 of the medicament delivery device 50 accommodated in the receiving compartment. The separation tool 24 is furthermore aligned with an interface between the first compartment 12 and the second compartment 24. Accordingly, movement of the tray 23, from the first position to the second position, will move the receiving compartment 22 and the medicament delivery device 50 accommodated therein towards the separation tool 24, which will cause the separation tool to interact with the medicament delivery device 50 at the interface between the first part 52 and the second part 54. In other words, the receiving compartment 22 and the separation tool 24 are movable in relation to each other such that interaction between the separation tool 24 and the medicament delivery device 50 received in the receiving compartment separates the first part 52 from the second part 54.

In the depicted exemplary embodiment, the receiving compartment 22 is movable relative to the separation tool 24, and the separation tool 24 is fixed in relation to the waste container 10, and also in relation to the top lid 28. A resiliently flexible member 21 is arranged to bias the receiving compartment 22, such that receiving compartment 22, i.e. the tray 23, is returned to the first position after disposal of the medicament delivery device 50.

An alternative configuration (not shown) is conceivable, wherein the receiving compartment 22 is fixed relative to waste container 10, and relative to the top lid 28, and wherein the separation tool 24 is movable relative receiving compartment 22.

The first part 52 and the second part 54 of the medicament delivery device may be attached to each other by breakable or separable members such as a label, e.g. a sticker glued to an outer circumferential surface of the medicament delivery device 50, thin plastic members, latches, snap-fit members, or friction-fit members, etc.

As shown in FIGS. 3-6, the separation tool 24 may be a cutting tool. The cutting tool comprises a sharp edge that that may sever a breakable attachment member, such as a label or thin plastic members, when the separation tool 24 interacts with the medicament delivery device 50.

Alternatively, the separation tool 24 may be a wedge-like member (not shown). As such, the wedge-like member is wedged between the first part 52 and the second part 54, forcing them apart, when the separation tool 24 interacts with the medicament delivery device 50.

At the end of the relative movement from the first position to the second position, the first part 52 and second part 54 are completely separated from each other. The receiving compartment 22 and the second slot 26 are aligned. The parts may fall through the second slot 26 on opposite sides of the separation tool, such that the first part 52 may fall into the first compartment 12 and the second part 54 may fall into the second compartment 54.

Other embodiments are conceivable, wherein the medicament delivery device 50 is inserted longitudinally into the waste container 10, either vertically or horizontally. In the vertical case, it may be necessary to implement a pushing member to separate the two parts since they do not spontaneously fall into the two separate compartments. The pushing member may be a resilient member, such as a spring, that biases one of the parts, laterally, away from the other part.

The first part 52 of the medicament delivery device 50 comprises a medicament delivery member, such as a needle, and a medicament container. The second part 54 may comprise an electronics unit, for instance a circuit, a transceiver module and a power cell, e.g. a battery. The interface between the first part 52 and the second part 54 is longitudinally positioned to match the longitudinal position of the separation tool 24 of the waste container 10.

A manner of using the waste container 10 will hereinafter be described, referring to FIGS. 4-7, which show a cross-section of the waste container 10 and the medicament delivery device 50. The cross-sectional plane is located at the longitudinal position of the interface between the first part 52 and the second part 54, i.e. at the longitudinal position of the separation tool 24.

Figure 4:
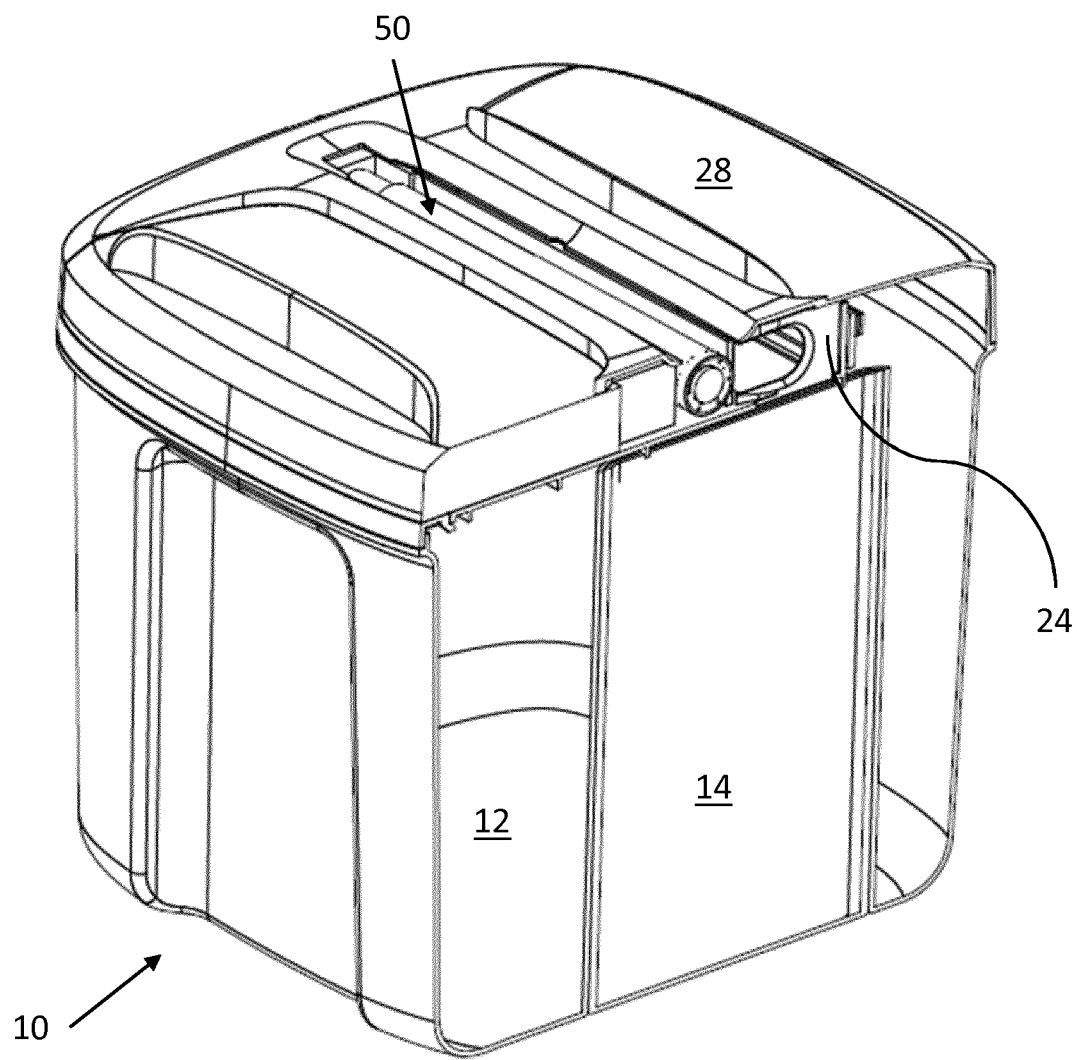
FIG. 4-6 a cross-sectional view of various operational states of the waste container and the medicament delivery device of FIG. 1

After a user has expended the contents of a medicament delivery device 50, the device is inserted into the first slot 29, such that it is accommodated in the receiving compartment 22, FIG. 4, which receiving compartment 22 is initially in the first position.

Figure 5:
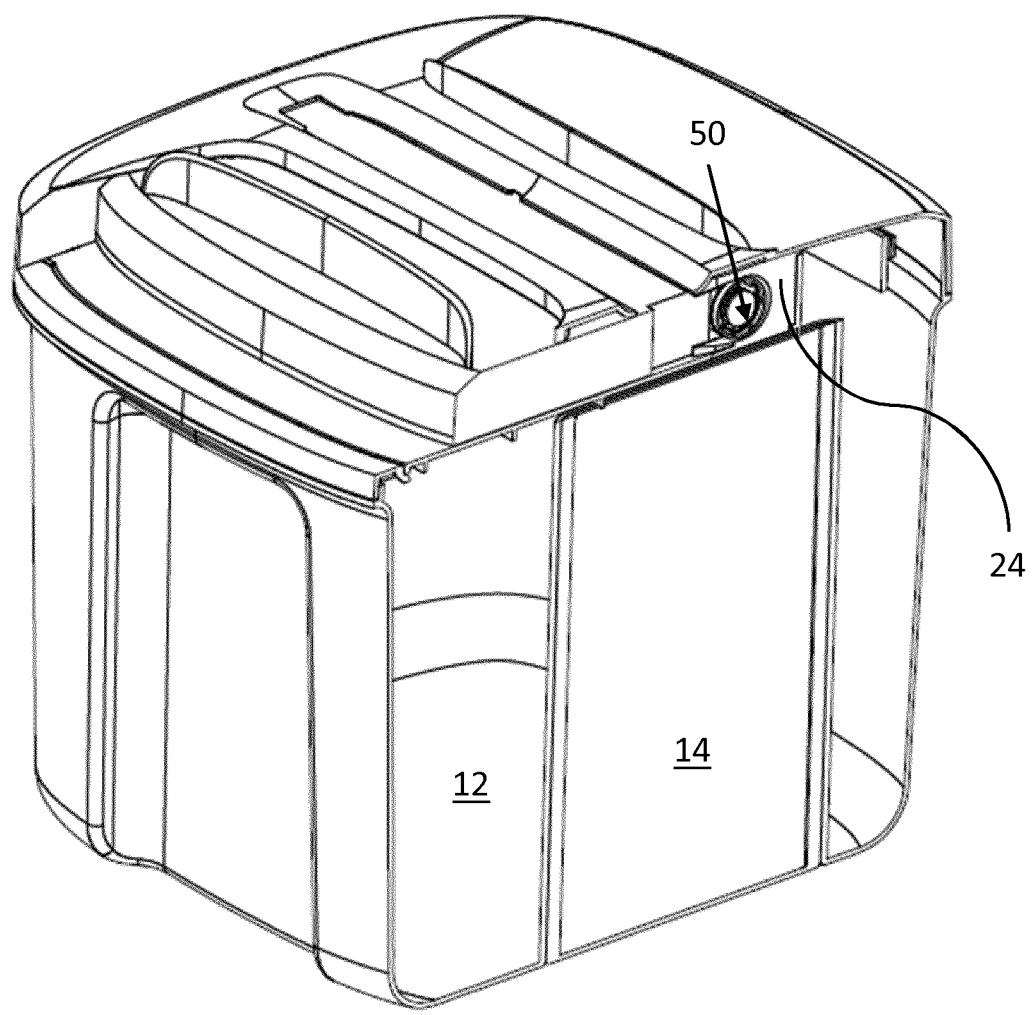

The user then pushes the tray 23 and the receiving compartment 22, together with the medicament delivery device 50, towards the second position and the separation tool 24. FIG. 5 shows an intermediate position, at an initial stage of interaction between the separation tool 24 and the medicament delivery device 50. An upper surface of the tray 23 covers the first slot 29, such that the first slot 29 is closed.

Figure 6:
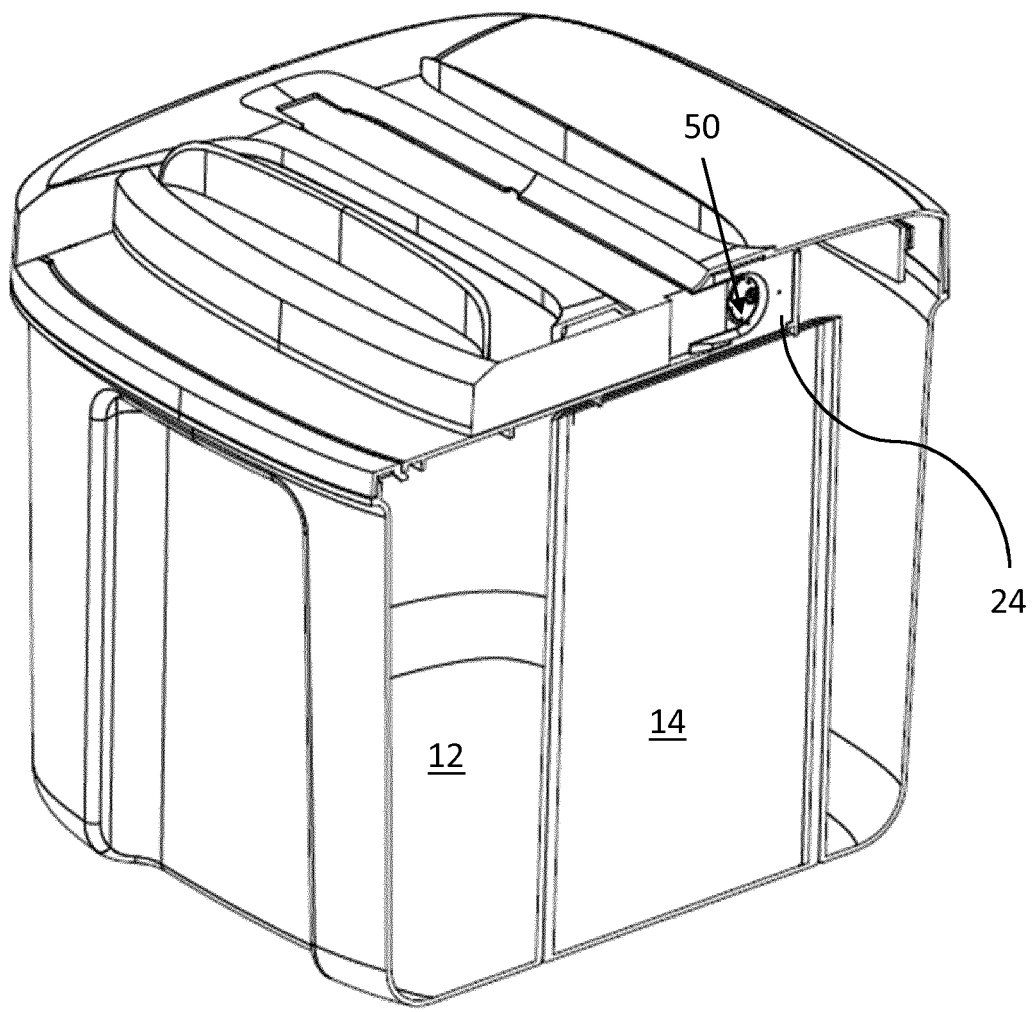
Figure 7:
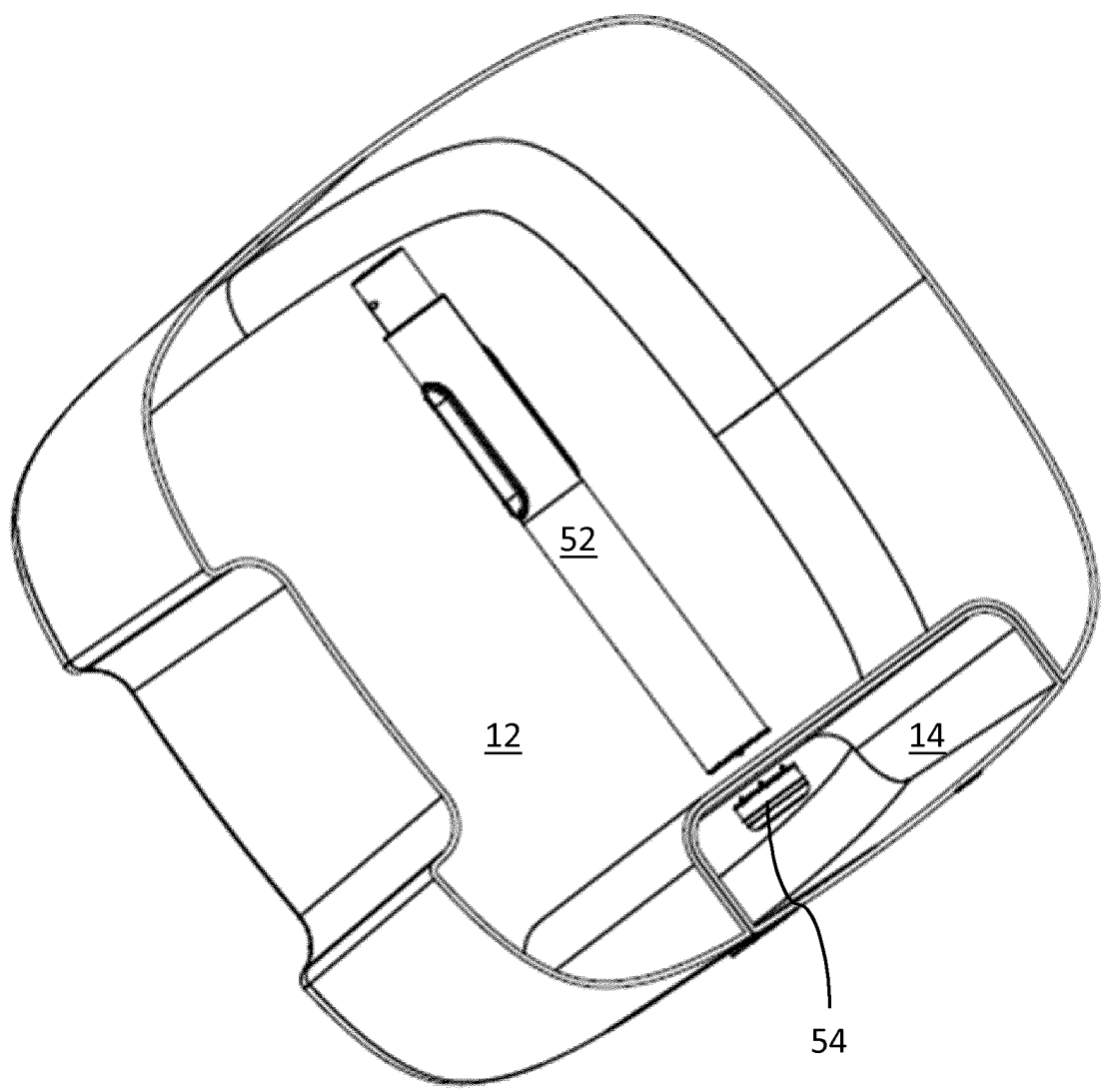
FIG. 7 a cross-sectional view the waste container and a resulting state of the medicament delivery device of FIG. 1

As the user continues to push the tray 23, the receiving compartment 22 and the medicament delivery device 50 towards the second position, the separation tool 24 separates the first part 52 of the medicament delivery device 50 from the second part 54, by cutting, or by pushing the parts apart. FIG. 6 shows how the separation tool 24 has reached approximately half-way through the medicament delivery device 50.

As the tray 23 and the receiving compartment 22 reach the second position, the separation operation is complete. The first part 52 and the second part 54 are completely separated from each other such that they fall through the second slot 26, on opposite sides of the separation tool 24, into the first compartment 12 and the second compartment 14, respectively. See FIG. 7. Since the second compartment 14, containing the second part 54, is detachable from the waste container the second part 14 may easily be recycled separately from the first part 12. In this way, batteries and electronics comprised in the second part 54 may conveniently be recycled while the hazardous components, such as needles and medicament containers are kept safe in the first compartment 12.

The invention claimed is:

1. A waste container for medicament delivery devices, which waste container comprises:
    a first waste compartment;
    a second waste compartment;
    a receiving compartment for accommodating a medicament delivery device inserted into the waste container; and
    a separation tool arranged to separate a first part from a second part of the medicament delivery device such that the first part is stored in the first waste compartment and the second part is stored in the second waste compartment,
    wherein at least one of the receiving compartment and the separation tool are movable in relation to the other such that interaction between the separation tool and the medicament delivery device received in the receiving compartment separates the first part from the second part, and
    wherein the separation tool is positioned above both the first waste compartment and the second waste compartment at an interface between the first waste compartment and the second waste compartment.

2. The waste container for medicament delivery devices according to claim 1,
    wherein the receiving compartment is movable relative to the separation tool.

3. The waste container for medicament delivery devices according to claim 2,
    wherein the separation tool is fixed in relation to the waste container.

4. The waste container for medicament delivery devices according to claim 3,
    wherein movement of the receiving compartment towards the separation tool moves the medicament delivery device, accommodated in the receiving compartment, towards the separation tool.

5. The waste container for medicament delivery devices according to claim 1,
    wherein the receiving compartment is fixed relative to the waste container.

6. The waste container for medicament delivery devices according to claim 5,
    wherein the separation tool is movable relative receiving compartment.

7. The waste container for medicament delivery devices according to claim 6,
wherein movement of the separation tool towards the receiving compartment is a movement of the separation tool towards the medicament delivery device accommodated in the receiving compartment.

8. The waste container for medicament delivery devices according to claim 1,
wherein the separation tool comprises a cutting tool.

9. The waste container for medicament delivery devices according to claim 1,
wherein the separation tool comprises a wedge-like member.

10. The waste container for medicament delivery devices according to claim 1,
wherein the waste container further comprises a removable lid assembly.

11. The waste container for medicament delivery devices according to claim 10,
wherein the receiving compartment and the separation tool are comprised in the lid assembly.

12. The medicament delivery device for disposal in the waste container according to claim 1,
which the first part and the second part of the medicament delivery device are separable from each other by disposal of the medicament delivery device in the waste container.

13. The medicament delivery device for disposal in the waste container according to claim 12,
wherein the first part and the second part are attached to each other by a breakable member.

14. The medicament delivery device for disposal in the waste container according to claim 12,
wherein the first part and the second part are attached to each other by a separable member.

15. The medicament delivery device for disposal in the waste container according to claim 13,
wherein the breakable member is a label.

16. The medicament delivery device for disposal in the waste container according to claim 14,
wherein the separable member is a snap-fit or friction-fit member.

17. The medicament delivery device for disposal in the waste container according to claim 12,
wherein the first part comprises a medicament delivery member and a medicament container.

18. The medicament delivery device for disposal in the waste container according to claim 17,
wherein the second part comprises an electronics unit.

19. The waste container for medicament delivery devices according to claim 1,
wherein the second waste compartment is detachable from the waste container.

* * * * *